(12) United States Patent
Koeppl

(10) Patent No.: US 10,120,100 B2
(45) Date of Patent: Nov. 6, 2018

(54) BODY SCANNER SYSTEM AND METHOD FOR SCANNING A PERSON

(71) Applicant: Rohde & Schwarz GmbH & Co. KG, Munich (DE)

(72) Inventor: Josef Koeppl, Zachenberg (DE)

(73) Assignee: Rohde & Schwarz GMBH & Co. KG, Munich (DE)

( * ) Notice: Subject to any disclaimer, the term of this patent is extended or adjusted under 35 U.S.C. 154(b) by 0 days.

(21) Appl. No.: 15/260,116

(22) Filed: Sep. 8, 2016

(65) Prior Publication Data

US 2018/0067043 A1    Mar. 8, 2018

(51) Int. Cl.
*G01V 8/10*    (2006.01)

(52) U.S. Cl.
CPC ...................... *G01V 8/10* (2013.01)

(58) Field of Classification Search
CPC ... G01N 21/3581; G01N 2201/11; G01V 8/10
See application file for complete search history.

(56) References Cited

U.S. PATENT DOCUMENTS

| | | | | |
|---|---|---|---|---|
| 6,057,761 | A * | 5/2000 | Yukl | A61B 5/0507 250/358.1 |
| 6,507,309 | B2 * | 1/2003 | McMakin | G01S 7/20 342/179 |
| 7,365,672 | B2 * | 4/2008 | Keller | G01N 21/3581 342/179 |
| 2003/0158482 | A1 | 8/2003 | Poland et al. | |
| 2012/0161265 | A1 * | 6/2012 | Hora | G01T 1/167 257/429 |
| 2014/0348417 | A1 * | 11/2014 | Moore | A61B 5/1075 382/154 |
| 2015/0154691 | A1 * | 6/2015 | Curry | G06Q 30/0643 705/27.2 |
| 2016/0051211 | A1 * | 2/2016 | Linev | A61B 6/4405 378/62 |
| 2016/0066811 | A1 | 3/2016 | Mohamadi | |
| 2016/0216371 | A1 * | 7/2016 | Ahmed | G01V 8/005 |

(Continued)

OTHER PUBLICATIONS

"Portable 3d body Scanner/Body Scanning Machine," 2015, [online], [retrieved on Jun. 9, 2017]. Retrieved from the internet: <https://www.alibaba.com/product-detail/2015-portable-3d-body-scanner-3d_60189738307.html>.*

(Continued)

*Primary Examiner* — Christine S Kim
(74) *Attorney, Agent, or Firm* — Schwabe, Williamson & Wyatt P.C.

(57) ABSTRACT

A body scanner system for scanning a person to be scanned is described. Said body scanner system comprises a scan unit which has at least one antenna for emitting electromagnetic waves and a separately formed platform for said person. Said body scanner system comprises a scanning state in which said person stands on said platform during scanning while said scan unit is emitting electromagnetic waves used for scanning said person. Said body scanner system is transportable wherein said scan unit is formed such that said platform is held by said scan unit in a transportation state of said body scanner system. Further, a method for scanning a person is described.

20 Claims, 5 Drawing Sheets

(56) References Cited

U.S. PATENT DOCUMENTS

2016/0291160 A1* 10/2016 Zweigle .................. G01S 17/89

OTHER PUBLICATIONS

"3D printed selfies now easier than ever with Fuboss full body 3D scanning system," Oct. 23, 2015, [online], [retrieved on Jun. 9, 2017]. Retrieved from the internet: <http://www.3ders.org/articles/20151023-3d-printed-selfies-now-easier-than-ever-with-fuboss-full-body-3d-scanning-system.html>.*
Styku 3D body scanner: [retrieved on Feb. 6, 2018]. Retrieved from the Internet: <URL: www.styku.com/bodyscanner>.*
Naked 3D body scanner: [retrieved on Feb. 6, 2018]. Retrieved from the internet: <URL: naked.fit>.*

* cited by examiner

BODY SCANNER SYSTEM AND METHOD FOR SCANNING A PERSON

TECHNICAL FIELD

The invention relates to a body scanner system and a method for scanning a person.

BACKGROUND OF THE INVENTION

In general, body scanners are used to scan a person wherein electromagnetic waves are emitted for scanning the human body. Hence, such body scanners usually comprise a scan unit which has at least one antenna for emitting the electromagnetic waves. However, body scanners can be used for different purposes.

For instance, a body scanner can be used for security purposes since objects on the body of the person can be detected which are covered by the clothes of the person. Usually, such body scanners are used at airports or other similar facilities. These body scanners are also called millimeter wave scanners if non-ionizing electromagnetic radiation in the extremely high frequency radio band (EHF band) are used.

Further, body scanners are also used for medical and fitness purposes. These body scanners are helpful instruments to assist a physician or a trainer, in particular to provide a 3D scan of the scanned person. Moreover, body scanners for fitness purposes can be used by the person himself in order verify his fitness state. For medical purposes, X-ray body scanners and CT body scanners are typically used whereas the body scanners used for fitness purposes may use electromagnetic radiation in the extremely high frequency radio band (EHF band) or in other frequency ranges allowing a scan of the human body without harming the person.

The body scanners are typically formed in cabins or they are permanently installed at the place where the measurements will be performed, in particular the scans. Accordingly, a person has to go to a physician, a gym and/or a fitness trainer in order to get scanned by such a body scanner. Thus, persons who are disabled or cannot move for other reasons do not have a chance to be scanned by such a body scanner as long as they do not buy their own one or they are transported to the physician, gym and/or fitness trainer.

SUMMARY OF THE INVENTION

The invention provides a body scanner system for scanning a person, in particular a patient to be examined, wherein said body scanner system comprises a scan unit which has at least one antenna for emitting electromagnetic waves and a separately formed platform for said person, said body scanner system comprising a scanning state in which said person can stand on said platform during the scanning whilst said scan unit is emitting electromagnetic waves used for scanning said person, said body scanner system being transportable wherein said scan unit is formed such that said platform is held by said scan unit in a transportation state of said body scanner system.

The invention is based on the finding that a body scanner can be made mobile as the body scanner system is formed by separate parts which can be attached to each other such that the whole body scanner system can be transported easily. In particular, the scan unit and the platform are separately formed from each other and formed such that they can be combined for transportation purposes. The body scanner system can be converted into its transportation state in which the platform is held by and attached to the scan unit. Hence, it is possible to transport the whole body scanner system to a person in order to scan this person at his home or any other place without the need of buying an own body scanner.

Furthermore, a rental body scanner system can be provided which can be rented for a certain time, particularly on a daily basis.

As the body scanner system can be transported, a disabled person does not need to be transported to a physician, gym and/or fitness trainer in order to get scanned by the body scanner system. Instead the physician, fitness trainer or any other third person having the required knowledge may come to the person in order to carry out the scanning by using the portable body scanner system. In addition, the person himself can carry out the scanning by operating the body scanner system on his own.

Generally, the platform has a surface on which the person stands during the scan. This surface is inter alia driven by a motor such that it rotates during the scanning. Then, the person standing on the surface rotates during the scan with respect to the separately assembled scan unit emitting the electromagnetic waves whilst the person rotates. Accordingly, the person is linearly rotated in a horizontal plane such that a 360° image is generated.

The electromagnetic waves emitted by the scan unit impinge on the person to be scanned. The electromagnetic waves may be reflected and sensed by a sensor unit which is also provided in the scan unit of the body scanner system. Accordingly, a scan device is formed comprising the scan unit and the sensor unit.

Alternatively or supplementary, the electromagnetic waves impinging on the person to be scanned or other electromagnetic currents originating from the body scanner system induce electromagnetic pulses in the body of the person wherein these electromagnetic pulses can also be detected by the body scanner system for analysis purposes.

According to an aspect, said body scanner system has a handle for transportation purposes in its transportation state. Thus, the mobile body scanner system is easy to transport as the handle is gripped. The handle facilitates pulling or pushing the body scanner system for transportation purposes.

According to another aspect, said body scanner system has a standby state in which said platform is held by said scan unit wherein said standby state is different to said transportation state, said handle being extracted in said transportation state with respect to its position in said standby state. Therefore, the body scanner system can be stored in a very compact state since the platform is held by the scan unit and the handle is in a more compacted state than it is in its scanning or transportation positions. Accordingly, the volume of the whole body scanner system is minimized in its standby state. The body scanner system can be temporarily stored since less space is required. Particularly, it is not necessary to fully occupy one room just for the installation of a body scanner as would be the case if the body scanner was provided in a cabin or permanently installed. For instance, the body scanner system can be assembled and disassembled if necessary such as other fitness devices, for instance spinning bikes. Thus, the scans can be performed in the living room and, afterwards, the body scanner system is brought in its standby state such that it can be stored in a closet or cabinet.

Further, the dimensions of said scan unit and said platform are changeable, in particular the height is adjustable, said scan unit and said platform each having a transportation position and a scanning position. The separately formed platform and scan unit can be extracted and/or unfolded such that they are converted from their transportation positions into their scanning positions and the other way around. Thus, a compacting body scanner system is established due to the separately formed platform and scan unit which dimensions are changeable independently from each other.

Particularly, the sizes of said scan unit and said platform are reduced in their transportation positions with respect to their scanning positions. This ensures that the body scanner system can be transported easily since the whole body scanner system has a small volume in its transportation state.

According to an aspect, the platform comprises at least one post being movable with respect to a surface of said platform on which said person stands during the scan. The post can be used during the scanning for conducting electromagnetic pulses which occur while the person is exposed to the electromagnetic waves during the scanning. For instance, the post is foldable with respect to the surface on which the person stands during the scanning. This ensures that the size of the platform, in particular its height, can be reduced. The volume of the platform is noticeably minimized in its transportation position.

Furthermore, a retainer can be movably connected with said post, said retainer being contacted by said patient during the scanning. The retainer is used to ensure that the person remains in its position during the scan in order to guarantee that the scan provides optimal results. Further, the retainer and the post may be electrically connected to each other in order to ensure that an electromagnetic connection is established between the retainer contacted by the person and the platform. The platform may have a processing unit for processing the data received. Alternatively, the data received are sent to a processing unit via a communication interface provided in the platform. As the retainer is movably connected with the post, it is ensured that the retainer can be moved with respect to the post which ensures that the whole platform can be minimized with regard to its volume when it is converted into its transportation state.

According to an aspect, the retainer functions as said handle for said body scanner system in its transportation state. Therefore the retainer is used as retaining bar for the person during the scan and it doubles as handle for the whole body scanner system in its transportation state. The person transporting the body scanner system uses the retainer as the handle for pulling and/or pushing the body scanner system in its compact state.

Further, the scan unit and/or the platform may comprise first and second connection elements respectively which are used to fixedly connect said scan unit and said platform with each other in the transportation state of the body scanner system. This ensures that the platform does not drop off or disengage from the scan unit during transportation as the scan unit and the platform are fixedly connected to each other. For instance, a clip or any other mechanical connection is provided in order to ensure a fixed connection which can be detached easily. Therefore, a detachable connection is provided by the first connection elements and/or the second connection elements.

Moreover, the scan unit may have a scan portion comprising the at least one antenna. The scan portion houses the at least one antenna emitting the electromagnetic waves which are used to examine and/or scan the person staying on the platform. It has to be ensured that the scan unit is assembled such that the scan portion faces the person staying on the platform.

The scan portion may comprise at least two scan portion elements which are connected to each other such that said scan portion is adjustable in height. The scan portion elements can be slidable connected to each other such that the height may be adjusted by a relative movement of both scan portion elements relative to each other. Accordingly, a telescope-like scan portion is provided. This ensures that the transportation state of the scan unit has a lower height than the scan unit has in its scanning state. The slidable scan portion elements ensure that the height of the scan unit, in particular the scan portion, can be adjusted providing a scan unit having a reduced volume in its transportation state and in its standby state with respect to its height in the scanning state.

Furthermore, the scan unit may comprise a transportation portion having a bearing surface for said platform in said transportation state of said body scanner system. The bearing surface is used to hold the platform during the standby and the transportation states. Accordingly, the platform is placed on the bearing surface which substantially corresponds to a loading area of a sack truck.

The transportation portion may comprise at least two wheels for transportation purposes. Accordingly, the body scanner system is mobile and its transport is facilitated since the body scanner system can be easily moved due to the wheels, in particular by pushing or pulling the body scanner system. As already mentioned, the scan unit of the body scanner system corresponds substantially to a sack truck in its transportation state wherein the platform is placed on the corresponding loading area formed by the bearing surface.

According to one embodiment, the scan portion is releasably connected to the transportation portion. Thus, the scan unit may also be formed by separate parts which can be disassembled. Accordingly, the whole body scanner system may comprise three different parts, namely the platform, the scan portion as well as the transportation portion wherein the scan portion and the transportation portion can be assembled to form the scan unit, in particular for transportation purposes and/or for moving the scan portion.

According to another embodiment, one of the scan portion elements and the transportation portion are formed integrally with each other. The other scan portion element is nested in the scan portion element integrally formed with the transportation portion ensuring a telescopic movement of the scan portion for adjusting its height. The other scan portion element may be detachable connected to the scan portion element such that it can be separated. For instance, the other scan portion element comprises the scanning elements, in particular any sensors and antennas used for scanning the person.

The scan portion may be substantially perpendicular to said transportation portion and said scan portion doubles as an abutting surface for said platform in said transportation state of said body scanner system. Hence, the platform is placed on the bearing surface of the transportation portion whereas the platform leans against the scan portion during transportation and in the standby state of the body scanner system. This ensures that the platform is held by the scan unit safely.

Furthermore, the platform may comprise at least one movable stand. The movable stand can be used to adjust the height of the platform as well as to compensate unevenness of the floor on which the platform is placed. Preferably, three stands are provided in order to improve the stability of the platform. The stands can be moved such that the volume of the platform is reduced in its transportation state, in particular the length and the width of the platform.

According to another aspect, the scan unit and/or said platform may comprise a battery unit. Thus, it is possible to perform the scans without the need of electricity at the place where the scanning is intended to be performed. It is possible to use the transportable body scanner system outside, for instance for demonstration purposes or in the garden.

Alternatively or supplementary, the body scanner system has a power plug. The power plug can be used to connect the body scanner system to a power supply for operating purposes, in particular to a housing grid or a public grid. Accordingly, the body scanner system is operated by power obtained via the power plug. Furthermore, the power plug can be used to charge the battery unit(s).

The invention also provides a method for scanning a person with a body scanner system, in particular a body scanner system according to claim 1, said body scanner system comprising a scan unit which has at least one antenna for emitting electromagnetic waves and a separately formed platform for said person, wherein said person stands on said platform during the scanning whilst said scan unit is emitting electromagnetic waves used for scanning said person, and wherein said platform rotates during the scanning. Thus, it is ensured that a person to be scanned by the body scanner system is scanned from all sides as the person standing on the platform rotates, in particular by 360°, due to the rotation of the platform during the scanning. Accordingly, the emitted electromagnetic waves impinge on all portions of the body as the body is rotated such that each portion of the body faces the scan unit during the scanning. Hence, a 3D image of the person can be determined.

BRIEF DESCRIPTION OF DRAWINGS

The invention will now be described with reference to preferred embodiments which are shown in the enclosed drawings. In the drawings, FIG. 1 schematically shows a body scanner system according to a first embodiment in its scanning state.

DETAILED DESCRIPTION

Figure 1:
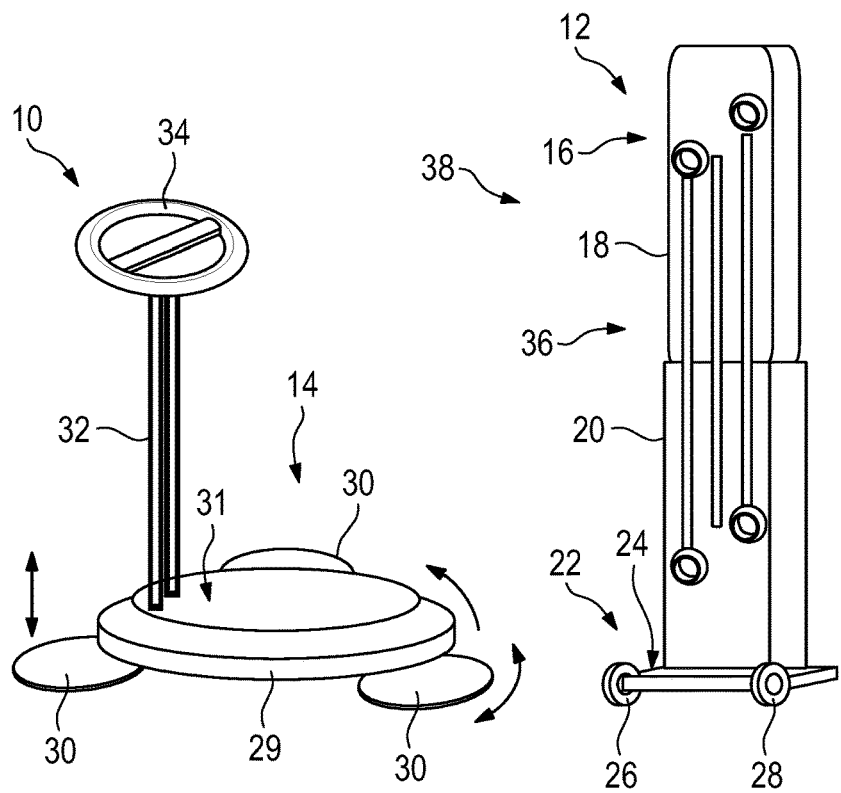

In FIG. 1, the body scanner system 10 is shown in its scanning state in which a person can be scanned by the body scanner system 10.

The body scanner system 10 comprises a scan unit 12 as well as a separately formed platform 14 on which a person stands while the scan is performed.

During the scanning, the scan unit 12 emits electromagnetic waves which are used to scan and/or analyze the person standing on the platform 14. The emitted electromagnetic waves can be reflected and/or absorbed by the person standing on the platform 14 as will be described later.

For emitting the electromagnetic waves, the scan unit 12 has a scan portion 16 which comprises at least one antenna for emitting the electromagnetic waves. Particularly, the scan portion 16 comprises an antenna array having several antennas which are used for emitting electromagnetic waves.

In the shown embodiment, the scan portion 16 comprises at least two scan portion elements 18, 20 which are movably nested within each other such that the height of the scan unit 12 is adjustable. Accordingly, the scan portion elements 18, 20 can be moved in a slidable manner with respect to each other. Therefore, the scan portion 16 and the scan unit 12 can be adjusted in a telescopic manner. This will be described later with respect to FIG. 2.

Furthermore, the scan unit 12 has a transportation portion 22 comprising a bearing surface 24 as well as two wheels 26, 28 which ensure that the scan unit 12 can be moved easily, in particular pulled and/or pushed.

Figure 4:
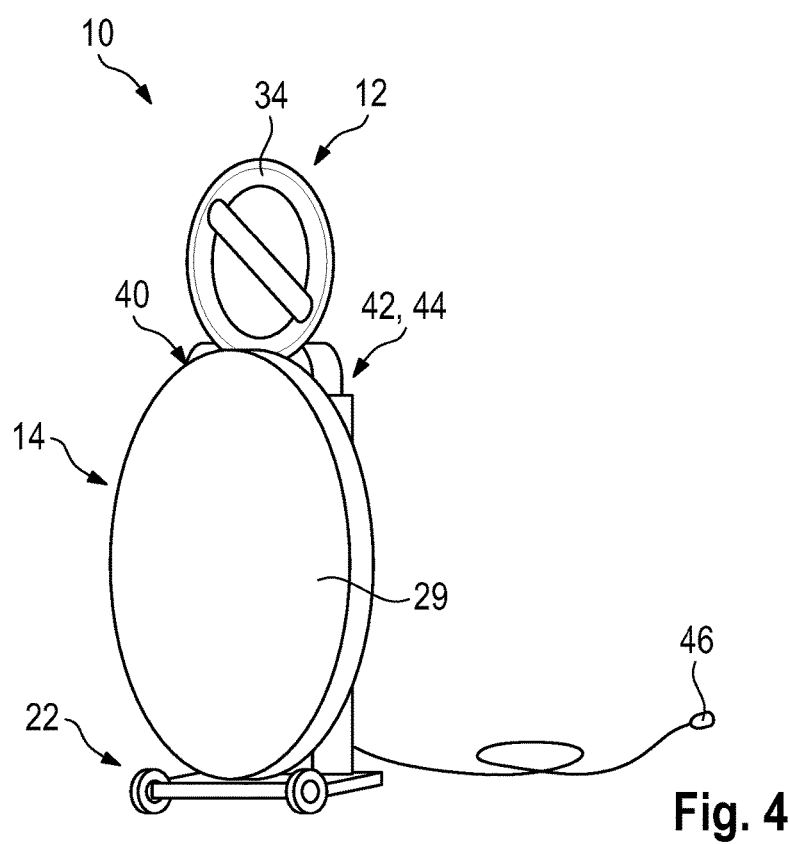
FIG. 4 shows the body scanner system according to a second embodiment in its standby state.
Figure 5:
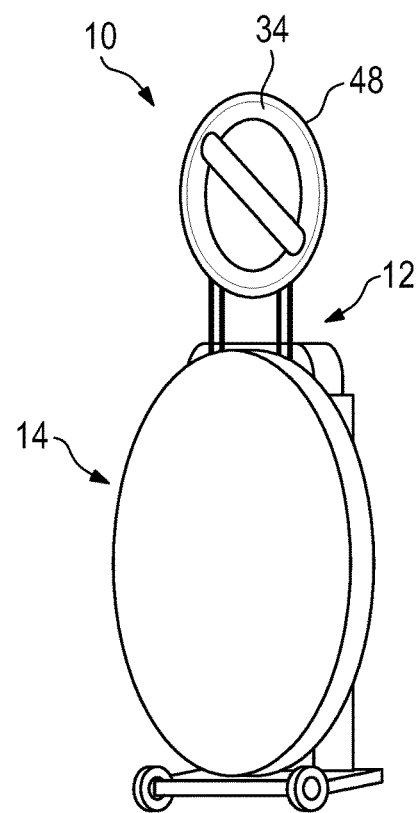
FIG. 5 shows the body scanner system of FIG. 1 in its transportation state.

The separately formed platform 14 can be placed on the bearing surface 24 of the transportation portion 22 during the standby and transportation states of the body scanner system 10 which are shown in FIGS. 4 and 5 and will be described later.

In the shown embodiment, the platform 14 comprises a main body 29 and three stands 30 attached to the main body 29, in particular its bottom side. The stands 30 are used to adjust the height of the platform 14 and to balance any unevenness of the floor on which the platform 14 is placed. This is also indicated by the arrow extending in vertical direction in FIG. 1.

Further, the curved arrow indicates that the stands 30 can be moved with respect to the main body 29. This ensures that the platform 14 can have a transportation position in which the stands 30 are displaced such that they are not visible in a view from above on the platform 14. Accordingly, the length and width of the platform 14 can be minimized with respect to the scanning position shown in FIG. 1.

On the topside of the platform 14, the main body 29 has a surface 31 on which the person to be scanned stands during the scanning process.

Moreover, the platform 14 comprises a post 32 and a retainer 34 which are moveably connected to each other such that their relative positions can be changed as will be described later with respect to FIG. 2.

During the scan, the person to be scanned stands on the platform 14, in particular the surface 31, and holds the retainer 34. The scan unit 12 emits electromagnetic waves which are used for scanning and/or examining the person standing on the platform 14 whilst the platform 14 rotates as indicated by the curved arrow, in particular the main body 29 and the surface 31 rotate. The rotation ensures that the emitted electromagnetic waves impinge the whole body of the person such that a 3D scan of the person is obtainable as the person rotates by 360° or more.

The electromagnetic waves may be reflected and sensed by a sensing unit 36 which is also housed in the scan unit 12 such that a scan device 38 is formed. This scan device 38 emits electromagnetic waves and senses the reflective portions in order to produce the 3D scan model of the person.

The frequency of the used wavelength, in particular electromagnetic radiation in the extremely high frequency radio band (EHF band), ensures that the person to be scanned can wear clothes during the scan since the electromagnetic waves penetrate the clothes such that information about the body of the person is obtainable.

Furthermore, electrodes can be provided in the retainer 34 and/or on the surface 31 such that further information about the person to be scanned can be gathered by using the body scanner system 10. Inter alia for this purposes, the retainer 34 and the post 32 are electrically conductive such that generated electromagnetic pulses are transmitted to the main body 29 of the platform 14 which might comprise a processing unit and/or a communication interface in order to communicate with a computer and/or the scan unit 12. The gathered information and/or data can be processed accordingly in order to produce the 3D scan model of the person.

Alternatively or supplementary, the emitted electromagnetic waves can be absorbed at least partly by the person and generate electromagnetic pulses which are sensed by the body scan system 10, in particular via the electrodes mentioned above.

Figure 2:
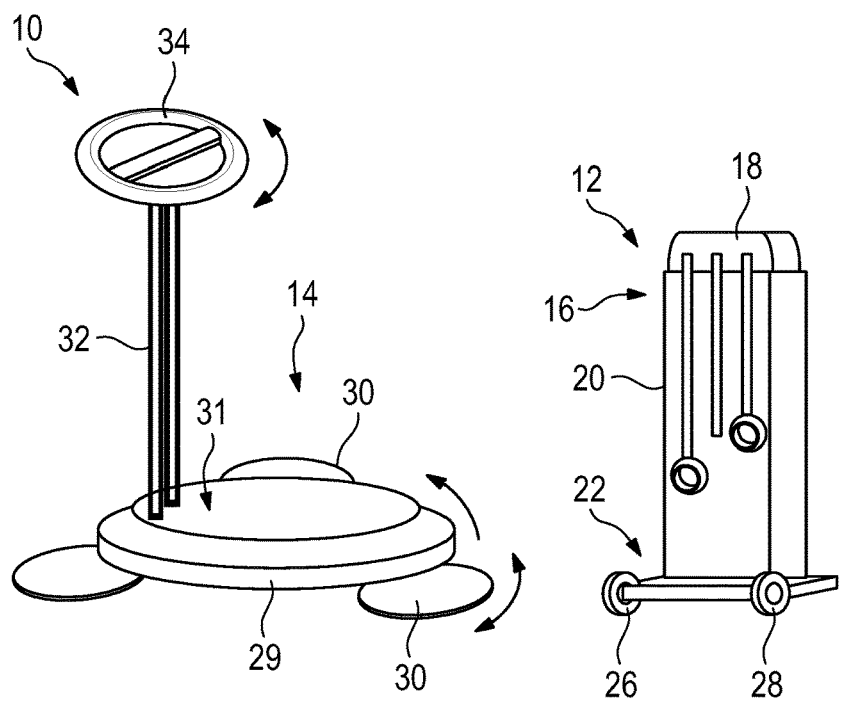
FIG. 2 shows the body scanner system of FIG. 1 in an intermediate state between the scanning state and its standby state.

As shown with respect to FIG. 2, the scan unit 12 can be adjusted in height since the scan portion elements 18, 20 are slidably connected to each other. Accordingly, the height of the scan unit 12 can be substantially halved when the scan unit 12 is brought into its standby or transportation position as shown in FIG. 2 with respect to the height in its scanning position as shown in FIG. 1.

Further, it is already indicated in FIG. 2 by the curved arrow that the retainer 34 is movably connected with the post 32 such that its position can be changed with respect to its position in the scanning state of the body scanner system 10. As already described, the stands 30 are also movably disposed at the bottom side of the platform 14, in particular the main body 29, which is also indicated by the curbed arrow in FIG. 2.

Figure 3:
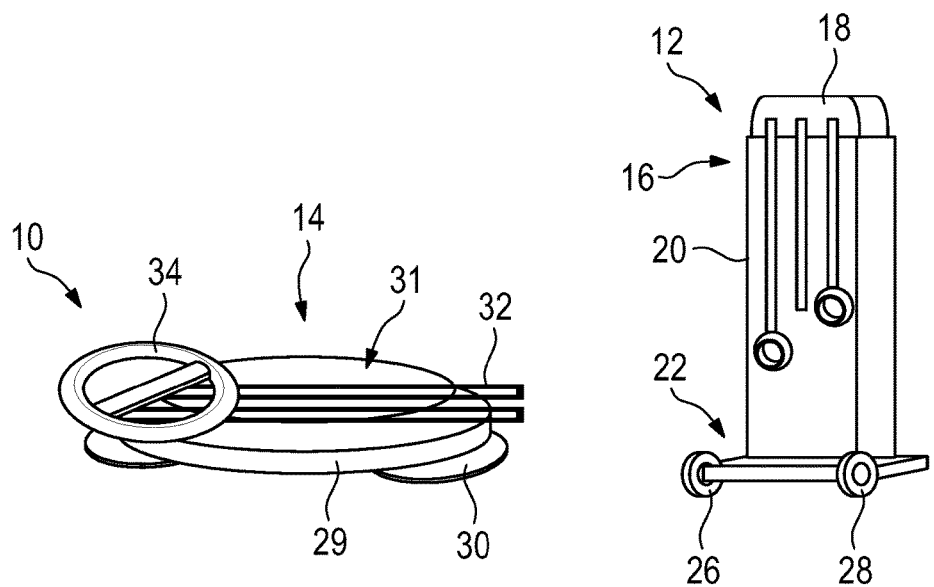
FIG. 3 shows the body scanner system of FIG. 1 in another intermediate state.

In FIG. 3, another intermediate state of the body scanner system 10 is shown in which the post 32 has been folded with respect to the main body 29 of the platform 14 in order to be in plane with the platform 14, in particular the surface 31 of the platform 14. Thus, the volume of the platform 14 is reduced, in particular the height of the platform 14, with respect to the height in the scanning position in which the post 32 extends substantially perpendicular from the surface 31 of the platform 14 in a vertical direction.

In FIG. 4, the body scanner system 10 is shown in its standby state. In this state, the platform 14 is held by and attached to the scan unit 12 such that the volume of the body scanner system 10 is reduced to a minimum.

The platform 14 is placed on the bearing surface 24 of the transportation portion 22 of the scan unit 12 such that it leans against the scan portion 16 which now doubles as an abutting surface 40 for the platform 14, in particular the lower scan portion element 20 as the upper one 18 is nested within the lower one 20 in the standby and transportation states.

Accordingly, the abutting surface 40 is substantially formed by the lower scan portion element 20.

For this reason, the lower scan portion element 20 may not comprise any scanning elements like sensors for sensing reflected electromagnetic waves and/or antennas for emitting electromagnetic waves which might be damaged by the platform 14 in the standby state.

Generally, the sensors can be provided by antennas, particularly by the same antennas used for emitting the electromagnetic waves wherein the antennas are controlled such that they act as emitting antennas and receiving antennas.

For safety reasons, the platform 14 and/or the scan unit 12 may have first and second connection elements 42, 44 respectively which are used to detachably connect the platform 14 to the scan unit 12 in the transportation state of the body scanner system 10. Accordingly, it is ensured that the platform 14 cannot drop off or detach from the scan unit 12 during transportation. The connection elements 42, 44 may be detachable mechanical elements such as clips.

In the shown embodiment, the scan unit 12 comprises a power plug 46 in order to electrically connect the body scanner system 10 to electricity, in particular to a housing grid.

In general, the power plug 46 can be used during the scan in order to provide the required power to the body scanner system 10, in particular the scan unit 12.

Alternatively or supplementary, the body scanner system 10 comprises at least one battery unit such that the body scanner system 10 can be operated wireless. The battery unit can be provided in the scan unit 12 for supplying the scan portion 16 with the required power. Another battery unit may be provided in the platform 14 in order to supply the electrodes and/or a processing unit with the required power.

Accordingly, the power plug 46 can also be used for charging the battery unit(s). Thus, the body scanner system 10 comprises a power socket for receiving the power plug 46.

Further, it is to be noted that the stands 30 are not visible in FIG. 4. According to one embodiment, the stands 30 are arranged at the bottom side of the main body 29 and not shown in FIG. 4.

Alternatively, the stands 30 can be received by pocket-like receptacles provided in the main body 29, in particular in the circumferential side, wherein the stands 30 are hinged such that they can be swiveled in or out of the pocket-like receptacles.

In FIG. 5, the body scanner system 10 is shown in its transportation state in which the retainer 34 is extracted with respect to its position in the standby state which becomes obvious when comparing FIGS. 4 and 5.

The extracted position of the retainer 34 can be established by a relative movement of the retainer 34 with respect to the stand 30. Alternatively or supplementary, the stand 30 is moved with respect to the surface 31 of the platform 14. Generally, the extracted position of the retainer 34 ensures that the body scanner system 10 can be transported more comfortable. This is comparable to a suitcase having a telescopic handle.

Thus, the retainer 34 acts as a handle 48 of the body scanner system 10 in its transportation state.

Further, it can be provided that the connection elements 42, 44 may be only activated such that a connecting function is established when the retainer 34 is extracted into its transportation position which is shown in FIG. 5.

Accordingly, a mechanism is provided which couples the retainer 34 and the connection elements 42, 44. This mechanism ensures that the platform 14 can be easily removed from the scan unit 12 in the standby state as the connection elements 42, 44 are not activated and the platform 14 only leans against the abutting surface 40.

In general, the body scanner system 10 is movable and transportable such that the whole body scanner system 10 can be transported to a person to be scanned. Accordingly, the body scanner system 10 can be a rental one.

On site, the body scanner system 10 can be converted from its transportation state into its scanning state fast and easily.

Figure 6:
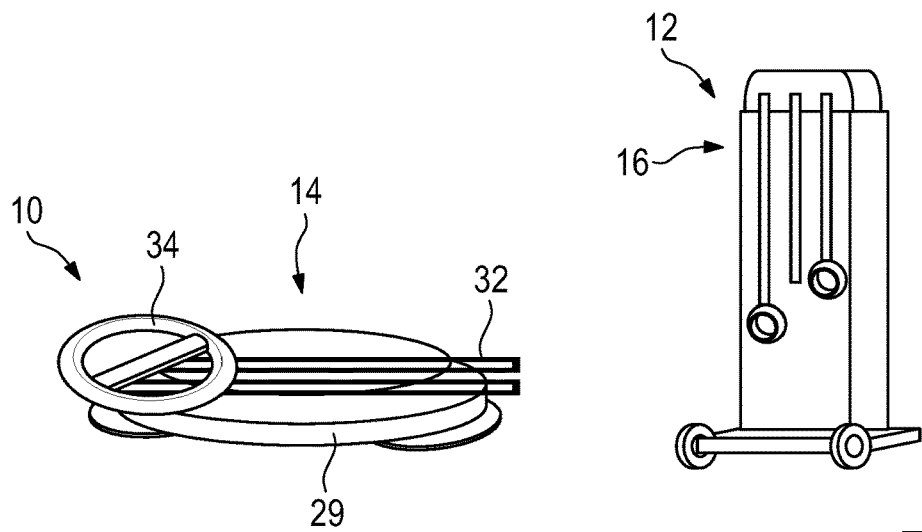
FIG. 6 shows the body scanner system of FIG. 1 in an intermediate state between the transportation state and the scanning state.

As shown in FIG. 6, the platform 14 is detached from the scan unit 12 such that the separate formed parts of the body scanner system 10 can be placed at the desired locations.

Figure 7:
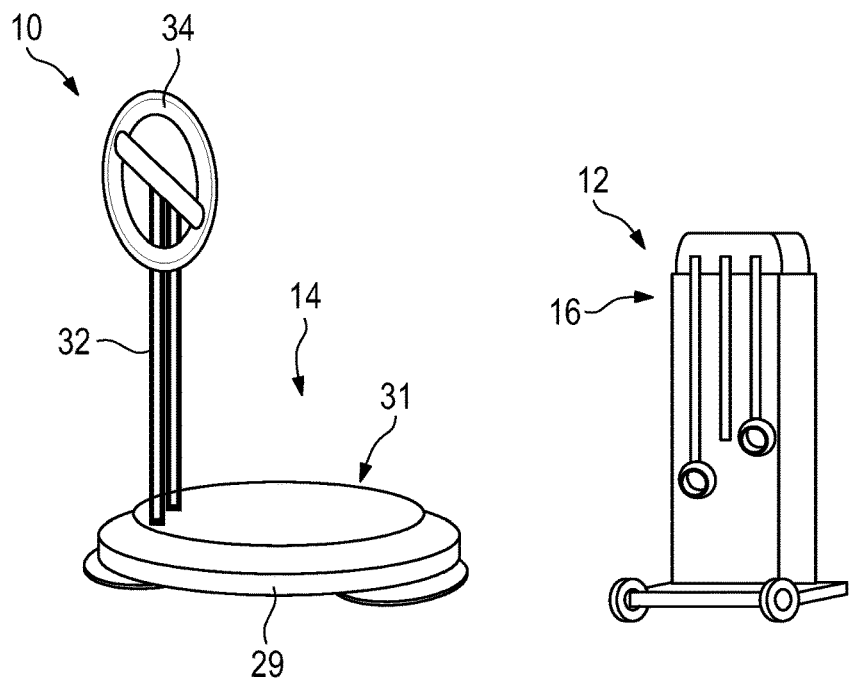
FIG. 7 shows the body scanner system of FIG. 1 in another intermediate state.

Afterwards, the post 32 is set up such that it extends substantially perpendicular to the surface 31 of the platform 14 as shown in FIG. 7.

Figure 8:
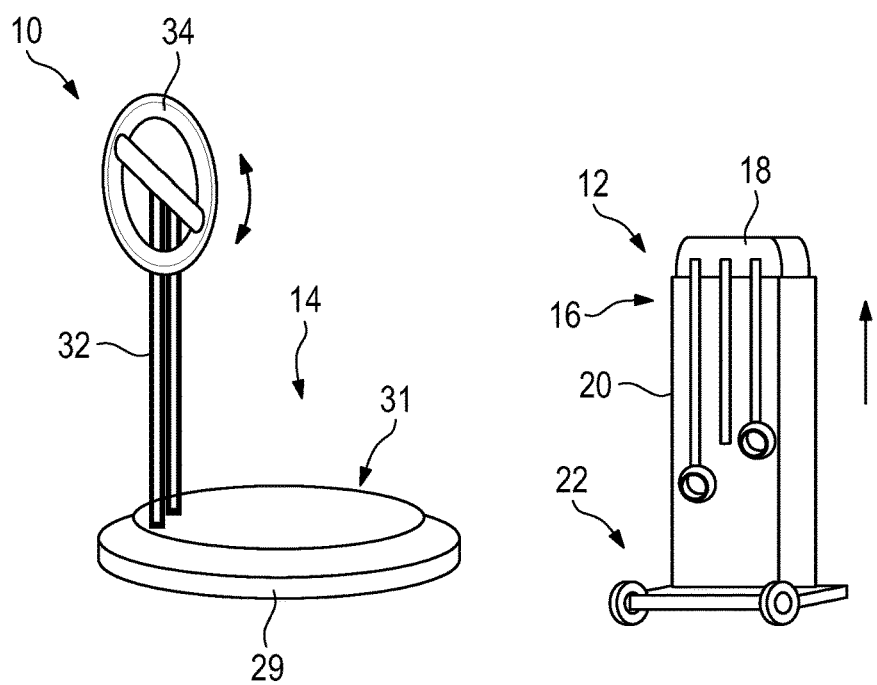
FIG. 8 shows the body scanner system of FIG. 1 in a further intermediate state.

As already indicated by the arrows in FIG. 8, the retainer 34 is turned with respect to the post 32 such that it is brought into its scanning position. In addition, the scan unit 12, in particular its scan portion 16, is slidably extracted such that the intended height of the scan unit 12 is reached which is required for the scan processes. Hence, the scan portion elements 18, 20 which are nested into each other can be moved with respect to each other in order to adjust the height. Particularly, the scan portion element 18 is extracted with respect to the scan portion element 20 which is connected to the transportation portion 22 of the scan unit 12.

Figure 9:
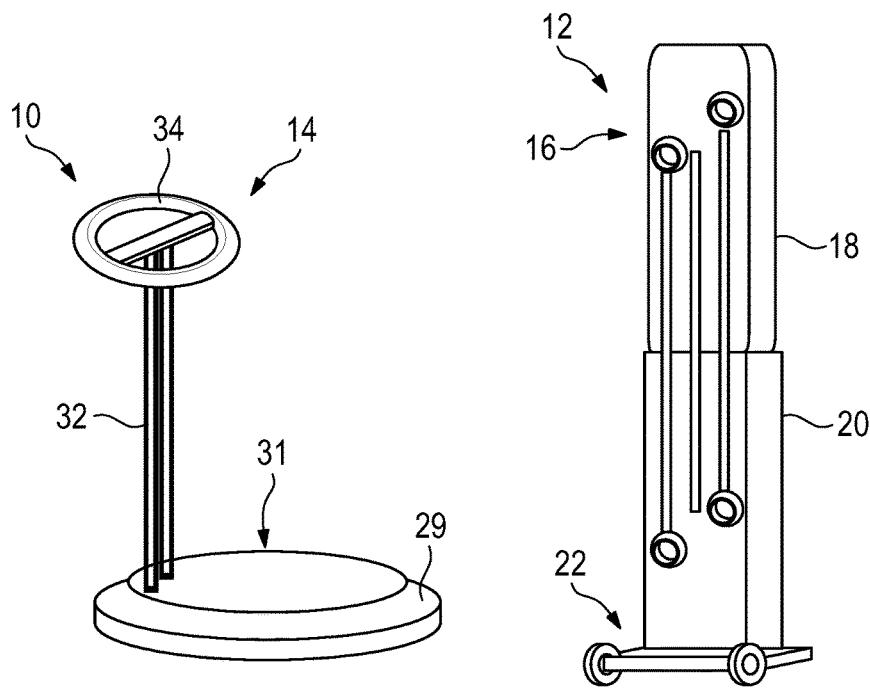
FIG. 9 shows the body scanner system of FIG. 1 in its scanning state.

Then, the whole body scanner system 10 is in its scanning position as shown in FIG. 9 which is substantially similar to the scanning position in FIG. 1 except for the fact that the stands 30 have not been used in order to adjust the height of the platform 14 and/or to balance any unevenness of the floor.

In the scanning position, the retainer 34 is latched such that an unintended relative movement of the retainer 34 with respect to the post 32 is prevented.

Further, the post 32 is also latched in its scanning position such that the post 32 also remains in its position during the scanning.

Figure 10:
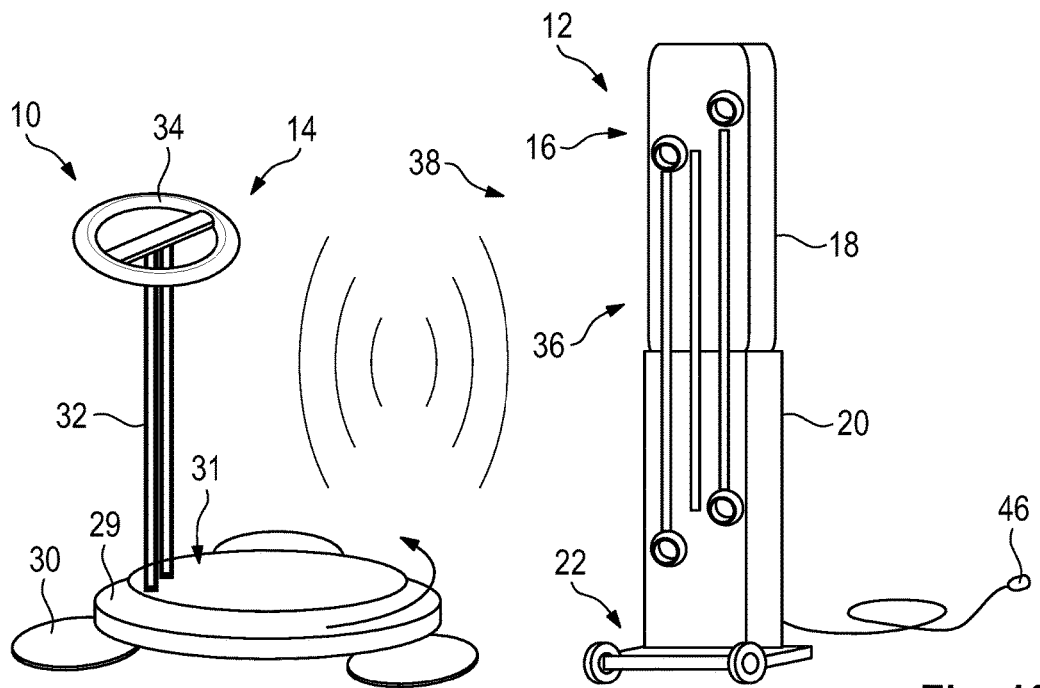
FIG. 10 shows the body scanner system of FIG. 4 during the scanning.

In FIG. 10, it is schematically shown that the body scanner system 10 uses electromagnetic waves for scanning a person standing on the platform 14, in particular on its surface 31. The electromagnetic waves are emitted by the scan unit 12, in particular the scan portion 16, wherein reflected portions of the electromagnetic waves are sensed by the sensing unit 36 housed in the scan unit 12, in particular the scan device 38.

Further, electromagnetic pulses may be sensed via the retainer 34 when a person stands on the surface 31 and touches the retainer 34.

As already mentioned, the platform 14 rotates as indicated by the curved arrow in FIG. 10 during the scanning process. Thus, the person standing on the platform 14 is scanned from each side such that a 360° scan image can be provided which data are processed to obtain a 3D model of the person.

As shown in FIG. 10, the body scanner system 10 can be operated by the power plug 46. As mentioned, battery units can also be used as shown in FIG. 1, for instance.

According to a special embodiment, the at least one antenna for emitting the electromagnetic waves is only provided in the upper scan portion element 18 such that the relative sensitive antenna element is protected in the standby and transportation states as the upper scan portion element 18 is covered by the other scan portion element 20 when both elements 18, 20 are nested within each other. Accordingly, the lower scan portion element 20 can be considered as being part of the transportation portion 22. In this special embodiment, the scan unit 12 comprises a scan portion 16 formed by the upper scan portion element 18 and a transportation portion 22 formed by the lower scan portion element 20, the bearing surface 24 and the wheels 26, 28.

FIGS. 1 to 10 reveal that the body scanner system 10 is easy to install. Hence, the person to be scanned himself can install the body scanner system 10 at home or at any other desired location without the need of a technician or service staff.

Accordingly, a body scanner system 10 is provided which can be used everywhere since the body scanner system 10 is mobile. Thus, the body scanner system 10 can be brought in its standby and transportation states and transported to the person to be scanned.

On site, the platform 14 is taken from the scan unit 12 and the body scanner system 10 is brought into its scanning state in which a person can be scanned by the body scanner system 10.

Thus, a flexible and mobile body scanner system 10 is provided.

As aforementioned, the body scanner system 10 can be used for medical, fitness or security purposes. Accordingly, the body scanner system 10 may be a medical scanner system, a fitness scanner system or a security scanner system each being mobile.

All necessary equipment for scanning the person can be housed in the scan unit 12, namely in one separately formed part of the body scanner system 10. Accordingly, a compact body scanner system 10 is provided.

The invention claimed is:

1. A body scanner system for scanning a person, said body scanner system comprising
    a scan unit which has at least one antenna for emitting electromagnetic waves that produce electromagnetic radiation in an extremely high frequency radio band (EHF band) and includes sensors that sense reflective portions of the emitted electromagnetic waves and produce a three dimensional model of the person, and
    a separately formed platform for said person,
    said body scanner system comprising a scanning state in which said person can stand on said platform during the scanning while said scan unit is emitting said electromagnetic waves used for scanning said person,
    said scan unit and said platform being formed such that they can be combined for transportation purposes, and
    said body scanner system being transportable wherein a connection element attaches said platform to said scan unit in a transportation state of said body scanner system, wherein:
    said scan unit has a scan portion comprising said at least one antenna,
    said scan portion is releasably connected to a transportation portion,
    said scan portion is substantially perpendicular to said transportation portion,
    said scan portion provides an abutting surface for said platform while folded in said transportation state of said body scanner system, and
    said platform while folded in the transportation state rests on a load bearing surface of said transportation portion substantially parallel with the scan portion.

2. The body scanner system according to claim 1, wherein said body scanner system has a handle for transportation purposes in said transportation state.

3. The body scanner system according to claim 2, wherein said body scanner system has a standby state in which said platform is held by said scan unit and wherein said standby state is different to said transportation state, said handle being extracted in said transportation state with respect to its position in said standby state.

4. The body scanner system according to 2, wherein a retainer functions as said handle for said body scanner system in said transportation state.

5. The body scanner system according to claim 1, wherein the sizes of said scan unit and said platform are reduced in said transportation state with respect to said scanning state.

6. The body scanner system according to claim 1, wherein said platform comprises at least one post being movable with respect to a surface of said platform on which said person stands during the scanning.

7. The body scanner system according to claim 6, wherein a retainer is moveably connected to said post, said retainer being contacted by said person during the scanning.

8. The body scanner system according to claim 7, wherein said retainer functions as a handle for said body scanner system in said transportation state.

9. The body scanner system according to claim 1, including first and second connection elements which fixedly connect said scan unit and said platform with each other in said transportation state of the body scanner system.

10. The body scanner system according to claim 1, wherein said scan unit comprises at least two scan portion elements which are connected to each other such that said scan portion is adjustable in height, and a first one of the scan position elements includes the antenna and telescopingly extends vertically up out of a second one of the scan portion elements during the scanning state and inserts vertically down into the second one of the scan portion elements during the transportation state.

11. The body scanner system according to claim 1, wherein said scan portion is releasably connected to a transportation portion.

12. The body scanner system according to claim 1, wherein said platform comprises at least one movable stand.

13. The body scanner system according to claim 1, wherein said scan unit and/or said platform comprise(s) a battery unit.

14. The body scanner system according to claim 1, wherein said body scanner system has a power plug.

15. The body scanner system according to claim 1, wherein:
said platform is operable in a detached, spaced apart, and independently positionable location relative to the scan unit, said platform including a post extending vertically up from a surface of the platform, a retainer attached to a top end of the post for grabbing onto by said person, and a motor for rotating the platform, and
said platform, post and retainer in a transportation state are foldable together into a substantially flat configuration for sitting on a horizontal transportation portion of the scan unit.

16. A body scanner system for scanning a person, said body scanner system comprising
a scan unit which has at least one antenna for emitting electromagnetic waves that produce electromagnetic radiation in an extremely high frequency radio band (EHF band) and includes sensors that sense reflective portions of the emitted electromagnetic waves and produce a three dimensional model of the person, and
a separately formed platform for said person,
said body scanner system comprising a scanning state in which said person can stand on said platform during the scanning while said scan unit is emitting said electromagnetic waves used for scanning said person,
said scan unit and said platform being formed such that they can be combined for transportation purposes, and
said body scanner system being transportable wherein a connection element attaches said platform to said scan unit in a transportation state of said body scanner system, wherein:
said scan unit has a scan portion comprising said at least one antenna,
said scan portion is releasably connected to a transportation portion, and
said transportation portion includes a bearing surface for said platform in said transportation state of said body scanner system.

17. The body scanner system according to claim 16, wherein said transportation portion comprises at least two wheels for transportation purposes.

18. The body scanner system according to claim 16, wherein said scan portion is releasably connected to said transportation portion.

19. The body scanner system according to claim 16, wherein said scan portion is substantially perpendicular to said transportation portion and said scan portion doubles as an abutting surface for said platform in said transportation state of said body scanner system.

20. A method for scanning a person with a body scanner system, with the following steps:
providing the body scanner system in a transportation or standby state having a reduced volume with respect to a scanning state, said body scanner system comprising a scan unit which has at least one antenna for emitting electromagnetic waves and a separately formed platform for supporting a person,
disassembling said scan unit and said platform from each other that are attached to each other in the transportation or standby state,
scanning said person during a scanning state with said scan unit while said person stands and is rotated by said platform and said scan unit is emitting electromagnetic waves used for scanning said person, wherein the scan unit has a horizontal transportation portion with wheels for transporting the scan unit, further with the following steps:
folding said platform into a substantially flat shape during a transportation state;
placing said folded platform on the transportation portion;
attaching said folded platform to the scan unit for wheeling both the folded platform and the scan unit together on the transportation portion during the transportation state;
detaching the folded platform from the scan unit during a next scanning state;
unfolding the platform; and
locating the unfolded platform at a spaced apart detached distance from the scan unit for scanning a next person.

* * * * *